US00PP32735P2

(12) United States Plant Patent
Hollister et al.

(10) Patent No.: US PP32,735 P2
(45) Date of Patent: Jan. 5, 2021

(54) ***DRYOPTERIS* PLANT NAMED 'HOLLASIC'**

(50) Latin Name: *Dryopteris wallichiana*
Varietal Denomination: Hollasic

(71) Applicant: Country Garden Plant Sales Ltd, Dorset (GB)

(72) Inventors: Robert Anthony Hollister, Dorset (GB); Gillian Hollister, Dorset (GB)

(73) Assignee: COUNTRY GARDEN PLANT SALES LTD, Dorset (GB)

( * ) Notice: Subject to any disclaimer, the term of this patent is extended or adjusted under 35 U.S.C. 154(b) by 0 days.

(21) Appl. No.: 16/873,375

(22) Filed: Mar. 30, 2020

(30) Foreign Application Priority Data

Dec. 13, 2019 (QZ) ..... PBR 2019/3392

(51) Int. Cl.
*A01H 5/12* (2018.01)
*A01H 9/00* (2006.01)

(52) U.S. Cl.
USPC ..... Plt./379
CPC ..... *A01H 9/00* (2013.01)

(58) Field of Classification Search
USPC ..... Plt./379
CPC ..... A01H 9/00
See application file for complete search history.

*Primary Examiner* — Kent L Bell
(74) *Attorney, Agent, or Firm* — Penny J. Aguirre

(57) ABSTRACT

A new cultivar of *Dryopteris wallichiana* plant named 'Hollasic' that is characterized by its fronds that are bronze and golden orange in color when young, its fronds that change in summer to bright golden yellow and finally green in summer and into fall, and its an upright mounded plant habit from a rosette of erect rhizomes.

2 Drawing Sheets

Botanical classification: *Dryopteris wallichiana.*
Variety denomination: 'Hollasic'.

CROSS-REFERENCE TO A RELATED APPLICATION

This application claims priority to European Community Plant Variety Office (CPVO) Plant Breeder's Rights Application No. 2019/3392 filed on Dec. 13, 2019, under 35 U.S.C. 119(f), the entire contents of which is incorporated by reference herein.

BACKGROUND OF THE INVENTION

The present invention relates to a new and distinct cultivar of *Dryopteris wallichiana*. The new *Dryopteris* will hereafter be referred to by its cultivar name, 'Hollasic'. 'Hollasic' is a new cultivar of wood fern for use as an ornamental plant.

The Inventors discovered the new cultivar in 2009 as a plug produced from spores from unnamed and unpatented plants of *Dryopteris wallichiana* in Dorset, United Kingdom.

Asexual propagation of the new cultivar was first accomplished by spores by the Inventors in 2014 in in Dorset, United Kingdom. The claimed plant is grown in isolation under controlled conditions from other spore producing plants to enable true to type reproduction. The characteristics of the new cultivar are stable and are reproduced true to type in successive generations of asexual propagation.

SUMMARY OF THE INVENTION

The following traits have been repeatedly observed and represent the characteristics of the new cultivar. These attributes in combination distinguish 'Hollasic' as a unique cultivar of *Dryopteris*.

1. 'Hollasic' exhibits fronds that are bronze and golden orange in color when young.
2. 'Hollasic' exhibits fronds that change in summer to bright golden yellow and finally green in summer and into fall.
3. 'Hollasic' exhibits an upright mounded plant habit from a rosette of erect rhizomes.

There are no known cultivars of *Dryopteris wallichiana* known to the Inventors. 'Hollasic' can be compared to the parent species *Dryopteris wallichiana* and typical plants of similar species; *Dryopteris erythrosora, Dryopteris lepdopoda*, and *Dryopteris affinis*. Plants of the parent species *Dryopteris wallichiana* differ from 'Hollasic' in having taller fronds, a more cone-shaped plant habit, fronds that are medium green in color when young and deep green in color when mature. Plants of *Dryopteris lepdopoda* differ from 'Hollasic' in having a creeping plant habit, fronds that are shorter and coppery pink in color when young and deep green in color when mature, and in being evergreen in colder winters. Plants of *Dryopteris affinis* differ from 'Hollasic' in having taller fronds, a more symmetrical plant habit, fronds that are pale green in color when young and medium green in color when mature.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website postings by Concept Plants, Thompson and Morgan, Seiont Nurseries, Crawford Ferns Dorset, and postings related to the clamed plants award in the Four Oaks Trade Show in 2018 (in which no sales occurred).

BRIEF DESCRIPTION OF THE DRAWINGS

The accompanying colored photographs illustrate the overall appearance and distinct characteristics of the new cultivar.

The plant in the photograph in FIG. 1 is about 10 years in age as grown outdoors in a 5-gallon container in Dorset, United Kingdom. The photograph in FIG. 1 provides a view of the young fronds of 'Hollasic'.

Figure 1:
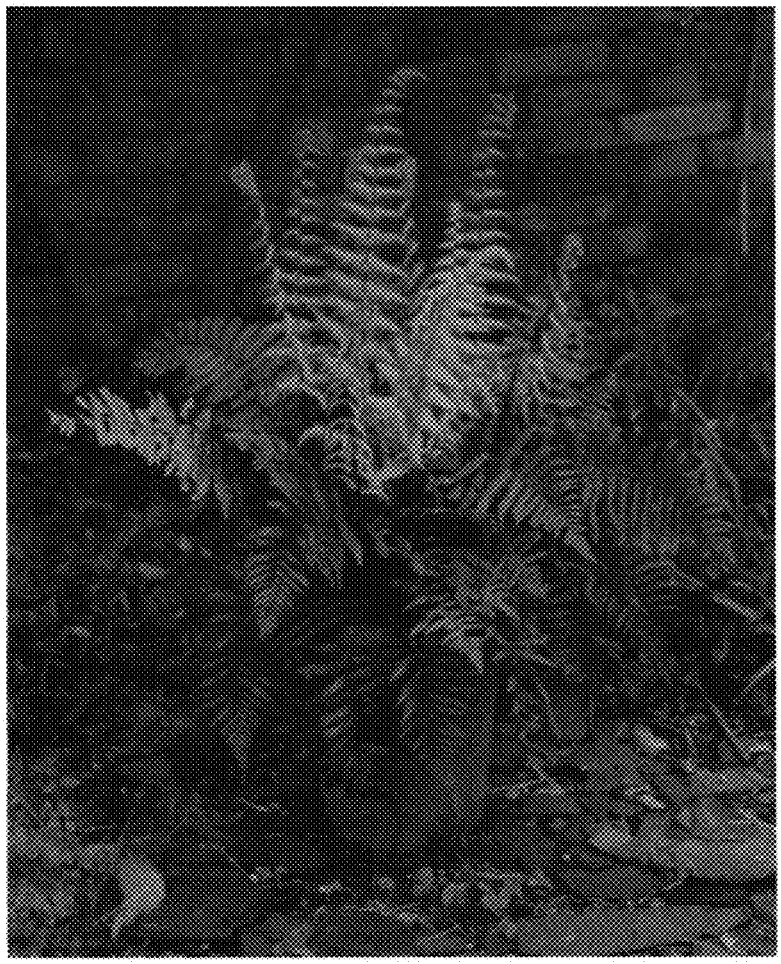
Figure 2:
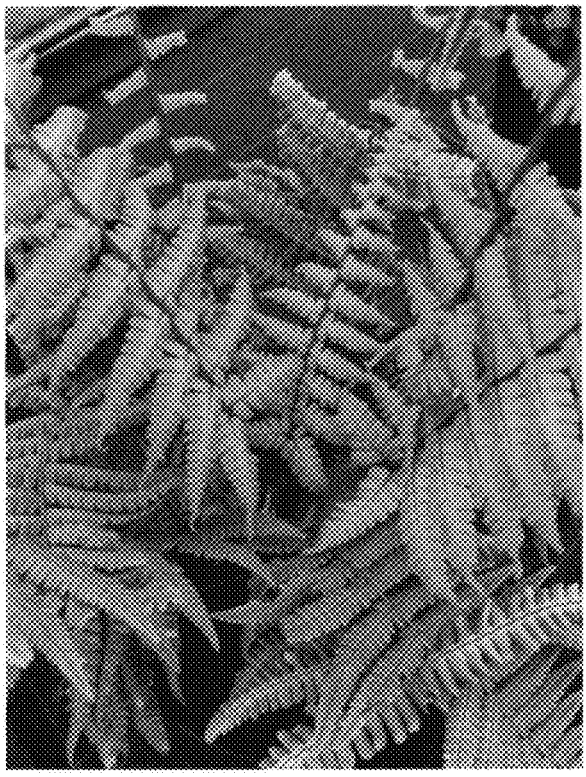
Figure 3:
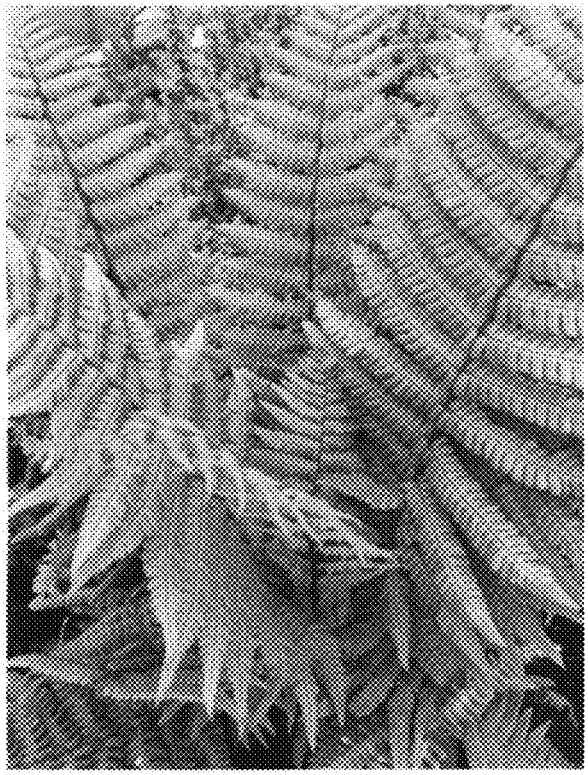

The photographs in FIG. 2 and FIG. 3 were taken of 3-year-old plants as grown in a cold greenhouse in 3-liter containers in Boskoop, The Netherlands. The photograph in FIG. 2 provides a view of the frond coloration in late spring to mid-summer of 'Hollasic'. The photograph in FIG. 3 provides a view of the frond coloration in late summer of 'Hollasic'.

The photographs are as close as possible with the digital photography techniques available, the color values cited in the detailed botanical description accurately describe the colors of the new *Dryopteris*.

DETAILED BOTANICAL DESCRIPTION

The following is a detailed description of two-year-old plants of the new cultivar as grown in a cold greenhouse in 10.5-cm containers in Boskoop, The Netherlands. The phenotype of the new cultivar may vary with variations in environmental, climatic, and cultural conditions, as it has not been tested under all possible environmental conditions. The color determination is in accordance with The 2007 Colour Chart of The Royal Horticultural Society, London, England, except where general color terms of ordinary dictionary significance are used.

General description:

*Plant type*.—Herbaceous perennial in colder regions and evergreen in mild conditions.

*Plant habit*.—Broadly spreading, upright.

*Plant size*.—Average of 28 cm in height, 27.9 cm in spread.

*Cold hardiness*.—At least in U.S.D.A. Zone 6.

*Diseases and pests*.—No susceptibility or resistance to diseases or pests has been observed.

*Root description*.—Fine and fibrous from rhizomes.

*Propagation*.—Spores from plants grown in isolation under controlled conditions from other spore producing plants for true to type reproduction.

*Growth rate*.—Moderate to high.

*Root development*.—An average of 15 weeks for fully root in a 1 cm cell from spore sowing.

Stem description: No stems or branches; fronds grow directly from the base; a rosette of erect rhizomes.

Frond description:

*Frond division*.—Compound, bipinnatifid.

*Frond arrangement*.—Alternate, fronds grow directly from the base.

*Frond size*.—Average of 20.3 cm in length, 13 cm in width.

*Frond/pinna base*.—Hastate.

*Frond quantity*.—An average of 15 per plant, 28 pinna per frond.

*Frond/pinna apex*.—Acute.

*Frond/pinna shape*.—Narrow to narrow deltoid.

*Frond/pinna surface*.—Both sides glabrous, upper surface glossy, lower surface matte.

*Pinna shape*.—Lanceolate.

*Pinna size*.—Average of 7.2 cm in length, 2.4 cm in width.

*Pinna margins*.—Deeply lobed into pinnules; average of 34 pinnules per pinna; 1.3 cm in length, 6 mm in width, broad oblong in shape, slightly falcate, slightly to moderately convex, praemorse apex, truncate base, fine serrate margins.

*Pinnule venation*.—Pinnate, upper surface color; 202A, secondary rachis color; 203D, lower surface color; 147B, secondary rachis color; 147B.

*Pinnule color*.—Young upper surface; 164A, changing to 165B, later turning to 152C, young lower surface; 164B, changing to 152C, mature upper surface; 143A, mature lower surface; 138B.

*Rachis*.—Average of 25.4 cm in length, 2.5 mm in diameter, upper surface 146A, lower surface between 146A and 147A, both surfaces densely covered with scaly hairs an average of 0.2 cm in length, N199C to N199D in color, secondary rachis moderately covered with scaly hairs; an average of 1 mm in length and 199A in color.

*Spores*.—An average of 7 per pinnule on the lower surface, round in shape, an average of 9 mm in diameter and 200A in color.

It is claimed:

1. A new and distinct cultivar of *Dryopteris* plant named 'Hollasic' as herein illustrated and described.

* * * * *